United States Patent [19]

Pacheco et al.

[11] 4,356,188
[45] Oct. 26, 1982

[54] 1-NAPHTHYL-ACETIC ACID DERIVATIVES AND THEIR THERAPEUTIC APPLICATIONS

[75] Inventors: Henri Pacheco, Lyons; Marie-Ange Descours-Saint-Martino, Villeurbanne; Démétré Yavordios, Chatillon, Chalaronne; Jean Koeberle, Villars les Dombes, all of France

[73] Assignee: Institut de Recherche Scientifique "I.R.S.", Chatillon sur Chalaronne, France

[21] Appl. No.: 173,171

[22] Filed: Jul. 28, 1980

Related U.S. Application Data

[63] Continuation-in-part of Ser. No. 6,511, Jan. 25, 1979, abandoned.

[30] Foreign Application Priority Data

Feb. 2, 1978 [FR] France .................. 78 02932

[51] Int. Cl.$^3$ .................. A61K 31/19; A61K 31/215; C07C 57/40; C07C 69/616
[52] U.S. Cl. .................. 424/317; 424/308; 560/100; 562/490
[58] Field of Search .................. 562/490; 560/100; 424/308, 317

[56] References Cited

U.S. PATENT DOCUMENTS 2,394,916  2/1946  JOnes .................. 71/107
4,009,197  2/1977  Fried et al. .................. 560/100

OTHER PUBLICATIONS

Woodward, Robert Burns et al., *Chemische Berichte*, vol. 86 (1953), pp. 594–601.
Wenham, A. J. M. et al., *Chemical Abstracts*, (1957), columns 3533 & 3534.

*Primary Examiner*—Natalie Trousof
*Assistant Examiner*—L. Hendriksen
*Attorney, Agent, or Firm*—Kenyon & Kenyon

[57] ABSTRACT

This invention relates to 1-naphthyl-acetic acid derivatives having the general formula:

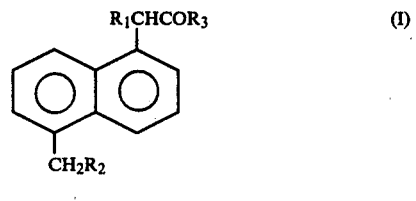

in which:
  $R_1$ is hydrogen atom or a straight- or branched-chain $C_{1-6}$ alkyl group,
  $R_2$ is a straight- or branched-chain alkyl group having 1-12 carbon atoms,
  $R_3$ is a hydroxy group, a $C_{1-6}$ straight- or branched-chain alkoxy group, and their pharmaceutically acceptable salts.

Said compounds have anti-inflammatory, anti-pyretic and analgesic activities and are free from ulcerogenic activity under the administration conditions.

6 Claims, No Drawings

1-NAPHTHYL-ACETIC ACID DERIVATIVES AND THEIR THERAPEUTIC APPLICATIONS

DESCRIPTION

This application is a Continuation-In-Part of U.S. Application Ser. No. 6,511, filed Jan. 25, 1979, now abandoned.

This invention relates to 1-naphthyl-acetic acid derivatives, to a process for their preparation and to their therapeutic applications.

Thus, this invention relates to a 1-naphthyl acetic acid derivatives having the general formula:

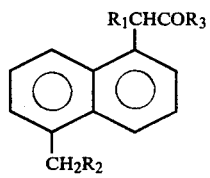
(I)

in which:
- $R_1$ is a hydrogen atom or a straight- or branched-chain $C_{1-6}$ alkyl group,
- $R_2$ is a straight- or branched-chain alkyl group having 1–12 carbon atoms,
- $R_3$ is a hydroxy group, a $C_{1-6}$ straight- or branched-chain alkoxy group, and their pharmaceutically acceptable salts.

Radical $R_1$ is typically a methyl, ethyl or propyl radical.

Radical $R_2$ is typically a methyl or isopropyl.

Radical $R_3$ is typically a hydroxy, methoxy, or ethoxy group.

This invention relates also to a process for the preparation of 1-naphthyl-acetic acid derivatives having the above-defined formula (I), comprising:

(a) reacting a compound of the formula:

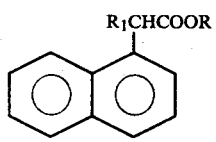
(II)

in which $R_1$ has the above-defined meaning and R is a $C_{1-6}$ straight- or branched-chain alkyl radical, with an acid chloride of the formula $R_2COCl$, in the presence of aluminum chloride and n in a solvent medium, to give a compound having the formula:

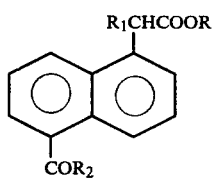
(Ia)

(b) hydrolyzing the ester having the formula (Ia) obtained in the preceding step, to give a compound having the formula:

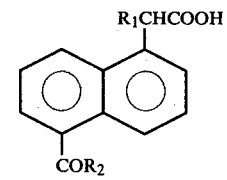
(Ib)

selectively reducing a compound of the formula (Ia) or (Ib) obtained in one of the preceding steps, to give a compound having the formula:

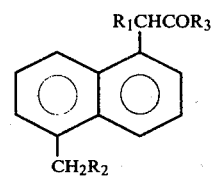
(I)

The solvent used for step (a) is typically methylene chloride.

In the course of step (b), hydrolysis of the ester is effected, for example, with an aqueous sodium hydroxide solution within a solvent medium such as refluxing ethyl alcohol.

To prepare compounds of the formula (I), a compound of the formula (Ia) or (Ib) is selectively reduced by means of the method according to Clemmensen, or typically by a Wolff Kishner reduction.

In the method according to Clemmensen, an amalgam is first prepared with Zn and mercuric chloride in concentrated hydrochloric acid medium, after which this amalgam is reacted with the compound to be treated, by refluxing within a suitable solvent such as acetic acid.

According to a modification, a Wolff Kishner reduction is used, comprising reacting hydrazine, with heating, in the presence of potassium hydroxyde and within a suitable solvent such as triethylene glycol with the compound to be converted.

To obtain esters of the formula (Ia), an acid of the formula (Ib) may also be esterified in conventional manner with the corresponding alcohol having the formula $R_3OH$.

The reactions obtained when R is a methyl radical are schematically represented below, to illustrate the process for the preparation of compounds of this invention.

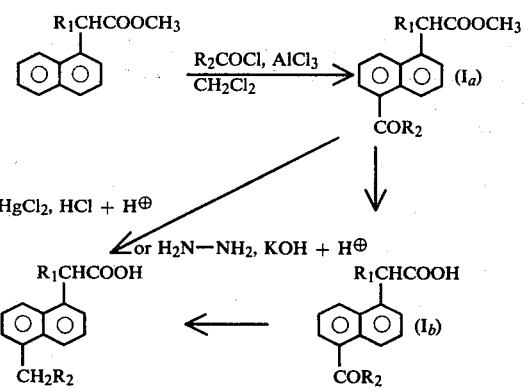

The following non-limiting Examples are given to illustrate compounds of this invention.

EXAMPLE 1

Preparation of [5-isobutyl-1-naphthyl]acetic acid Derivative 1

$R_1 = H$;

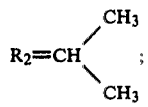

$R_3 = OH$.

(1) Preparation of methyl [5-isobutyryl-1-naphthyl]acetate

This compound corresponds to the general formula (I) in which $R_1 = H$,

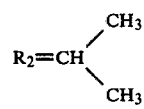

and $R_3 = OCH_3$, and is prepared according to the following reaction scheme:

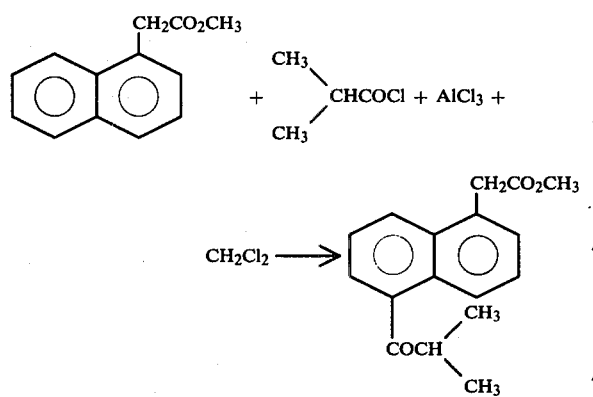

To a three-necked 1 liter flask, provided with a cooling device with $CaCl_2$ trap, an addition funnel and a thermometer (the flask being immersed in a water-bath maintained at room temperature) is added $CH_2Cl_2$ (250 cc) followed by $AlCl_3$ (200 g), with vigorous magnetic stirstirring. A mixture of $CH_2Cl_2$ (200 cc), methyl naphthyl acetate (100 g) and isobutyryl chloride (60 cc) is then added dropwise thereto. The addition is complete in about 4.5 hours, the temperature of the mixture remaining between 20° and 25° C. On completion of the addition, stirring is continued for a further 3.5 hours at room temperature, after which the reaction mixture is hydrolyzed by pouring over ice-water (1 liter). The resulting material is extracted with ether (2 liters). The organic phase is dried over $Na_2SO_4$ and the ether and $CH_2Cl_2$ are distilled off, to give a thick dark brown oil.

B.p.$_{1.5}$ = 175° C. Yield: 70% $n_D^{20}$ = 1.586

Vapor phase chromatography (VPC) shows the distilled product to be mixture of isomers: the isomer of the formula (Ia) is present in a highly major amount (90%).

(2) Clemmensen reduction of methyl [5-isobutyryl-1-naphthyl]acetate, according to the following reaction scheme:

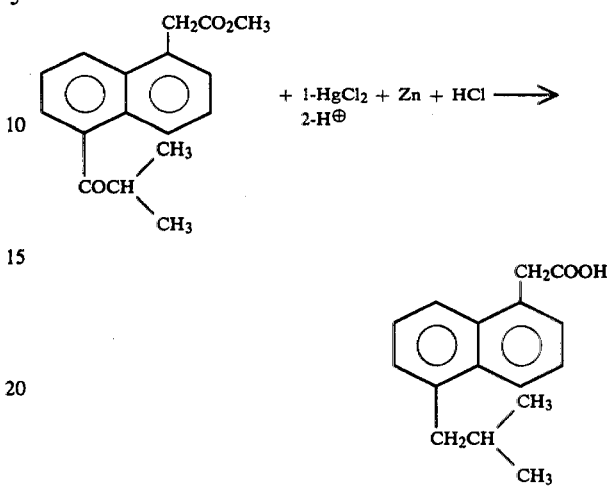

An amalgam is prepared as follows:

To 300 g zinc are added $H_2O$ (400 cc), $HgCl_2$ (23 g) and 12 N HCl (15 cc); the mixture is stirred very vigorously. It is then washed with 3×500 cc $H_2O$ and decanted, after which $H_2O$ (230 cc) and 12 N HCl (150 cc) are added.

To the resulting amalgam, is added methyl [5-isobutyryl-1-naphthyl]acetate (28 g) dissolved in acetic acid (50 cc) and the whole is refluxed for 48 hours, 12 N HCl (60 cc) being added thereto during the refluxing period. The material is then extracted with ether, and the zinc is rinsed with ether. The ether phase is washed with dilute sodium hydroxide (pH 7), the ester entrained is made free by acidification with HCl (pH 2), filtered and suction filtered. On crystallization from dilute acetate acid: M.p. = 172° C. Yield: 50%.

About 10% [5-isobutenyl-1-naphthyl]acetic acid forms during the reaction; it is removed during crystallization.

(3) Wolff Kishner reduction of methyl [5-isobutyryl-1-naphthyl]acetate according to the following reaction scheme

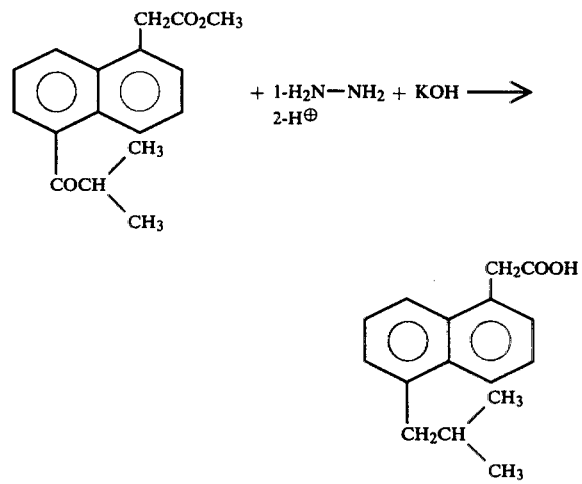

In all three-necked flask provided with a mechanical stirrer, a cooling device and a thermometer, are added 250 cc triethylene glycol followed by 95% potassium hydroxide (34 g), and the mixture is heated at 60° C. Methyl [5-isobutyryl-1-naphthyl]acetate (54 g) is then added thereto and the mixture is heated to a refluxing temperature of 120° C. Reflux is maintained for 1 hour, after which the mixture is left standing overnight.

Hydrazine (20 cc) is then added, while heating to 130° C., with vigorous stirring. Refluxing occurs; this is maintained for one hour.

Excess hydrazine and water (with added anti-foaming agent) is removed, and the material is refluxed at 200° C. for 4 hours.

The cooled mixture is poured over 500 ml water and is made acidic to about pH 2 with 12 N HCl. The resulting precipitate is suction filtered and crystallized. M.p.=172° C. Yield=50%.

EXAMPLE 2

Preparation of 2-[5-isobutyl-1-naphthyl]propionic acid Derivative 2

$R_1 = CH_3$;

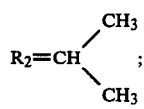

$R_3 = OH$ (1) Preparation of methyl 2-[5-isobutyryl-1-naphthyl]propionate $R_1 = CH_3$;

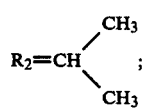

$R_3 = OCH_3$

This compound is prepared according to the following reaction scheme:

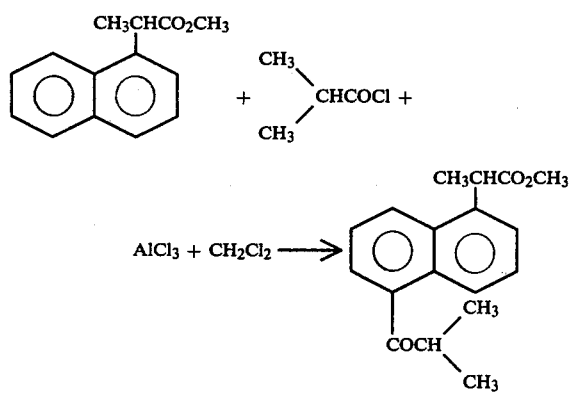

Under vigorous magnetic stirring, $CH_2Cl_2$ (125 cc) followed by $AlCl_3$ (60 g) are added to a 500 cc three-necked flask provided with a cooling device with $CaCl_2$ trap, a dropping funnel and a thermometer (said three-necked flask being immersed in a water-bath maintained at room temperature). Methyl 2-(1-naphthyl)-propionate (32.1 g) and isobutyryl chloride (18 cc) dissolved in $CH_2Cl_2$ (100 cc) are added thereto dropwise. The addition takes 2.5 hours. On completion of the addition, the ingredients are maintained in contact, with continued stirring. Hydrolysis is effected by pouring the reaction mixture over ice-water. The material is extracted with ether. The organic phase is washed over $Na_2SO_4$; the ether and $CH_2Cl_2$ are distilled off and the residual oil is distilled, to give the product named in the title.

$B.p._{1.5} = 185°$ C.; $n_D^{20} = 1.5755$. Yield=70%.

This product is a mixture of isomers, comprising a highly major amount of the isomer having the formula (Ia).

(2) The title compound is prepared by Clemmensen reduction of methyl 2-[5-isobutyryl-1-naphthyl]propionate obtained above, according to the following reaction scheme:

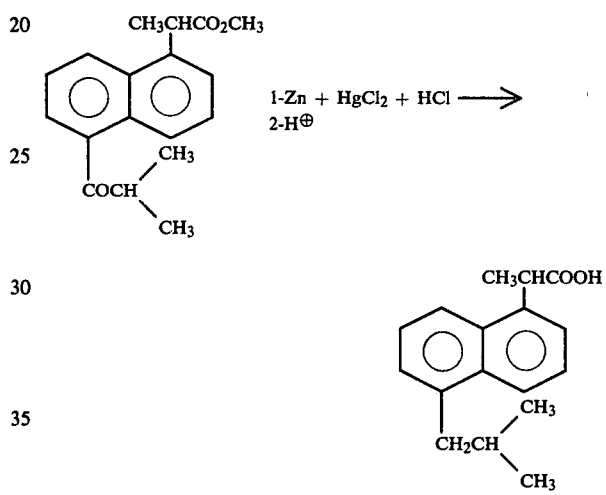

The amalgam is prepared as follows:

To zinc (148 g) are added mercuric chloride (7.4 g), $H_2O$ (140 cc) and 12 N HCl (7.4 cc) and the mixture is vigorously stirred. It is washed with 3×140 cc $H_2O$ and decanted. $H_2O$ (180 cc) and 12 N HCl (60 cc) are then added.

To the resulting amalgam is added methyl 2-[5-isobutyryl-1-naphthyl]propionate (10 g) dissolved in acetic acid (30 cc) and the mixture is refluxed for 72 hours, adding 12 N HCl (40 cc) during the refluxing period. The material is extracted with ether, the zinc is shaken with ether. The combined ether extracts are washed with dilute sodium hydroxide to pH 7 and the acid entrained is made free by acidification with HCl (pH2), and extracted with ether. The ether phase is dried over $Na_2SO_4$ and the ether is distilled off. The resulting acid is crystallized from pentane.

M.p. = 100° C. Yield = 50%.

The results of toxicological and pharmacological tests reported below demonstrate the useful activities of the derivatives of this invention.

Thus, this invention relates also to a therapeutic composition, having in particular anti-inflammatory, analgesic and anti-pyretic activities and which is free from ulcerogenic action, comprising, as active ingredient, an efficient amount of a compound of the formula (I) or therapeutically acceptable salts thereof, together with usual carriers and excipients.

1-Acute toxicity

Groups of 5 male CH. River rats, having an average weight of 125 g, kept on a water diet for 18 hours prior to the test, are orally administered the test materials, dissolved in neutral olive oil (1 ml/100 g), at dosages of 250–500–1000 and 2000 mg/kg.

The death rate is recorded 7 days after the administration: the lethal dose 50 (LD 50) is determined according to the method by Litchfield & Wilcoxon.

2-Anti-inflammatory activity

The test selected is the test of the carrageenin-induced plantar edema, according to Winter (Proc. Soc. Exp. Biol., 1961, 111, 544). Three groups of 10 rats, having an average weight of 125 g, are orally administered the various test materials, at dosages of 25–50–100 mg/kg, respectively. A fourth group (control) is administered only neutral olive oil (1 ml/100 g).

One hour after the treatment, 0.1 ml of a 1% carrageenin suspension is injected in the left plantar aponevrosis. The intensity of the edema is evaluated by immersing the inflamed paw in a mercury plethystometer. The percent inhibition of the edema is calculated from the mean value of the 7 determinations made hourly after carrageenin administration. The dosage which inhibits inflammation by 50% (ID 50) is determined in the same manner as previously described.

3-Anti-pyretic activity

After determination of the rectal temperature, rats are sub-cutaneously administered 1 ml/100 g of a 20% brewer's yeast suspension, and are put on a water diet.

17 hours later, their temperature is again determined. The mean increase of the rectal temperature, under such experimental conditions, is about 1.5° C.

The various test materials are then orally administered to groups of 10 rats (average weight: 140 g) at dosages of 25–50 and 100 mg/kg. A fourth group (control) is administered only olive oil (1 ml/100 g).

The temperature drop subsequent to the treatment is followed hourly, for a period of time of 5 hours. The mean percent inhibition is calculated by effecting the mean of the 5 determinations, with respect to the value 1.5° C. The ID 50, which is calculated as previously described, is the dose which reduces the fever by a factor of 50%.

4-Antalgic activity

The method used is that according to Sigmund and co-workers (Soc. Exp. Biol. Med. 1957, 95, 729) as modified by Hendershot & Forsaith (J. Pharm. Exp. Therap. 1959, 125, 237–240) and Lines & Gouret (J. Pharm. (Paris) 1972, 3, 513–515).

Intraperitoneal administration of 0.25 ml/20 g, in mice, of a 0.02% phenylbenzoquinone solution in 5% alcohol, produces the development of a pain syndrome which is characterized by writhing movements and by hollow flanks.

Treatment of groups of 10 male Ch. River mice (average weight: 20 g) at dosages of 25–50 and 100 mg/kg p.o. (a control group being administered only neutral olive oil; 0.5 ml/20 g) is effected 30 minutes prior to phenylbenzoquinone administration.

The ID 50 is calculated as previously indicated, from the percent inhibition of the spasms counted from the fifth to the tenth minute that follow the injection of the algogenic agent.

5-Ulcerogenic activity

The technique used is that according to Robert & Nezamis (Proc. Soc. Exp. Biol. Med., 1958,99,443–447) as modified by Lwoff (J. Pharmacol. (Paris) 1971, 2, 81–83).

Groups of 20 rats of Ch. River strain (average weight: 130 g) kept on a water diet for the 24 hours prior to the test, are orally administered the test materials, at dosages of 50–100–200–400 and 800 mg/kg. A reference group is administered only neutral olive oil, at a dosage of 1 ml/100 g.

Six hours later, the animals are sacrificed by bulbar trauma, after which their stomachs are cut out, opened along the great curvature and rated according to a scale from 0 to 3, according to the extent of the ulceration.

The ulceration index for each dosage is calculated according to the following formula:

$$\frac{\text{sum of scores} \times \% \text{ stomachs with ulcers}}{\text{number of animals}}$$

With this scoring method, a 100% ulceration index is equal to 300. The 50% ulcerogenic dosage (UD 50) is that which corresponds to an index of 150.

| Derivative n° | Acute toxicity LD 50 | Anti-inflammatory activity ID 50 | Anti-Pyretic activity ID 50 | Antalgic activity ID 50 | Ulcerogenic activity UD 50 |
|---|---|---|---|---|---|
| 1 | 600 | 15 | 0.7 | 24 | >800 |
| 2 | 130 | 5 | <1 | 4 | — |
| Naprosyne$^R$ (naproxen) | 290 | 3 | 4.1 | 10.6 | 43 |
| Brufen$^R$ (ibuprofen) | 780 | 38 | 12 | 9 | 220 |

TABLE 2

Ratios $\frac{\text{toxicity}}{\text{activity}}$ and $\frac{\text{ulcerogenic action}}{\text{activity}}$

| Ratio studied | Naproxene | Ibuprofene | Derivative 1 | Derivative 2 |
|---|---|---|---|---|
| Toxicity (LD 50 mg/kg P.O. rat) | | | | |
| Activity (ID 50 mg/kg P.O. rat) | | | | |
| Anti-inflammatory | $\frac{290}{3} = 96.7$ | $\frac{780}{38} = 20.5$ | $\frac{600}{15} = 40$ | $\frac{130}{5} = 26$ |
| Anti-pyretic | $\frac{290}{4.1} = 70.7$ | $\frac{780}{12} = 65$ | $\frac{600}{0.66} = 909$ | $\sim \frac{130}{1} = 130$ |

TABLE 2-continued

Ratios $\frac{\text{toxicity}}{\text{activity}}$ and $\frac{\text{ulcerogenic action}}{\text{activity}}$

| Ratio studied | Naproxene | Ibuprofene | Derivative 1 | Derivative 2 |
|---|---|---|---|---|
| Minimum ulcerogenic dosage* (mg/kg P.O. rat) Activity (ID 50 mg/kg P.O. rat) | | | | |
| Anti-inflammatory | $\frac{13.5}{3} = 4.5$ | $\frac{62}{38} = 1.6$ | $\frac{950}{15} = 63.3$ | — |
| Anti-pyretic | $\frac{13.5}{4.1} = 3.3$ | $\frac{62}{12} = 5.2$ | $\frac{950}{0.66} = 1439$ | — |

*Minimum ulcerogenic index = 40

The results of said investigations clearly demonstrate the low toxicity and the useful anti-inflammatory, anti-pyretic, antalgic and non-ulcerogenic properties of the derivatives of the formula (I), which are profitably administrable to humans, particularly for the treatment of inflammatory conditions.

The compounds of formula I may be formulated for oral administration as tablets, capsules and slurry. They may also be formulated as suppositories for rectal administration, and as injectable solutions for parenteral administration.

Each unit dose contains advantageously from 0.050 to 0.500 g active ingredient, the daily dosage regimen varying within the range from 0.100 to 1.250 g active ingredient.

Non-limiting examples of pharmaceutical formulations of the therapeutic composition are given below.

EXAMPLE 3-Tablets

| Derivative 3 | 0.250 g |
|---|---|
| Lactose | 0.200 g |
| Starch | 0.050 g |
| Polyvinyl pyrolidone | 0.010 g |
| Magnesium stearate | 0.005 g |

EXAMPLE 4-Capsules

| Derivative 3 | 0.250 g |
|---|---|
| Lactose | 0.050 g |
| Talc | 0.010 g |
| Silica | 0.005 g |
| Magnesium stearate | 0.010 g |

EXAMPLE 5-Oral suspension

| Derivative 3 | 5 g |
|---|---|
| Sucrose | 40 g |
| Glycerol | 10 g |
| Sodium carboxymethyl cellulose | 0.5 g |
| Avicel RC 591 | 0.5 g |
| Sorbic acid | 0.1 g |
| Flavor and water, sufficient to make | 100 ml |

EXAMPLE 6-Suppositories

| Derivative 3 | 0.250 g |
|---|---|
| Semi-synthetic glycerides, sufficient to make 1 suppository | 3 g |

EXAMPLE 7-Injectable solution

| Derivative 3 | 0.050 g |
|---|---|
| Benzylic alcohol | 0.2 ml |
| Propylene glycol, sufficient to make | 3 ml |

Having now described our invention what we claim as new and desire to secure by Letters Patent is:

1. A compound selected from the group consisting of 1-naphthyl-acetic acid derivatives of the formula:

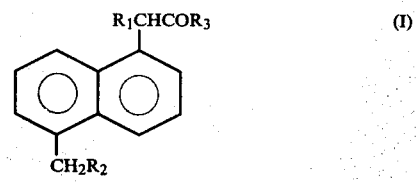

in which:
R$_1$ is selected from the group consisting of hydrogen and straight- and branched-chain C$_{1-6}$ alkyl groups,
R$_2$ is selected from the group consisting of straight- and branched-chain alkyl groups having 3–12 carbon atoms,
R$_3$ is selected from the group consisting of hydroxy, C$_{1-6}$ straight- and branched-chain alkoxy radicals and the pharmaceutically acceptable salt of acids of the formula (I).

2. [5-Isobutyl-1-naphthyl]acetic acid and its pharmaceutically acceptable salts.

3. 2-[5-Isobutyl-1-naphthyl]propionic acid and its pharmaceutically acceptable salts.

4. A method for treating a host with a therapeutic composition having anti-inflammatory, anti-pyretic, analgesic and non-ulcerogenic activities, comprising administering to said host an effective amount of a compound selected from the group consisting of 1-naphthyl-acetic acid derivatives of the formula:

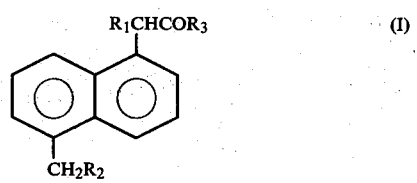

in which:
R$_1$ is selected from the group consisting of hydrogen and straight- and branched chain C$_{1-6}$ alkyl groups, $R_2$ is selected from the group consisting of straight- and branched-chain alkyl groups having 1–12 carbon atoms, $R_3$ is selected from the group consisting of hydroxy, $C_{1-6}$ straight- and branched-chain alkoxy groups, and the pharmaceutically acceptable salt of acids of the formula (I).

5. A therapeutic composition having anti-inflammatory, anti-pyretic, analgesic and non-ulcerogenic activities, comprising an effective amount of a compound selected from the group consisting of [5-isobutyl-1-naphthyl]acetic acid and its pharmaceutically acceptable salts, together with a pharmaceutically acceptable excipient.

6. A therapeutic composition having anti-inflammatory, anti-pyretic, analgesic and non-ulcerogenic activities, comprising an effective amount of a compound selected from the group consisting of 2-[5-isobutyl-1-naphthyl]propionic acid and its pharmaceutically acceptable salts, together with a pharmaceutically acceptable excipient.

* * * * *